(12) United States Patent
Scheller et al.

(10) Patent No.: US 8,241,321 B2
(45) Date of Patent: Aug. 14, 2012

(54) SURGICAL INSTRUMENT CONSTRUCTED BY ELECTRIC DISCHARGE MACHINING

(75) Inventors: Gregg D. Scheller, Wildwood, MO (US); Michael S. Poulsen, House Springs, MO (US)

(73) Assignee: Synergetics, Inc., O'Fallon, MO (US)

( * ) Notice: Subject to any disclaimer, the term of this patent is extended or adjusted under 35 U.S.C. 154(b) by 2800 days.

(21) Appl. No.: 10/820,330

(22) Filed: Apr. 7, 2004

(65) Prior Publication Data
US 2004/0193214 A1 Sep. 30, 2004

Related U.S. Application Data

(62) Division of application No. 10/167,914, filed on Jun. 12, 2002, now Pat. No. 6,772,765.

(51) Int. Cl.
*A61B 17/00* (2006.01)
(52) U.S. Cl. ...................................................... 606/207
(58) Field of Classification Search .................. 606/205, 606/207, 210
See application file for complete search history.

(56) References Cited

U.S. PATENT DOCUMENTS

| | | | |
|---|---|---|---|
| 4,693,246 A | 9/1987 | Reimels | |
| 4,761,028 A | 8/1988 | Dulebohn | |
| 4,793,218 A | 12/1988 | Jordan et al. | |
| 4,938,214 A * | 7/1990 | Specht et al. | 606/174 |
| 5,065,516 A | 11/1991 | Dulebohn | |
| 5,370,658 A | 12/1994 | Scheller et al. | |
| 5,463,917 A | 11/1995 | Kothe | |
| 5,584,845 A | 12/1996 | Hart | |
| 5,588,832 A * | 12/1996 | Farzin-Nia | 433/4 |
| 5,893,846 A | 4/1999 | Bales et al. | |
| 5,980,556 A | 11/1999 | Giordano et al. | |
| 5,981,895 A | 11/1999 | Grace et al. | |
| 6,616,683 B1 * | 9/2003 | Toth et al. | 606/207 |

FOREIGN PATENT DOCUMENTS

| | | |
|---|---|---|
| JP | 02-251329 | 10/1990 |
| JP | 08-090344 | 4/1996 |
| NL | 9200491 | 10/1993 |

OTHER PUBLICATIONS

Supplementary European Search Report, dated Mar. 31, 2010, for PCT No. PCT/US0310262.
Andreas E. Guber, Nicola Giordano, Michael Loser, Paul Wieneke, Karlsruhe Und Tuttlingen; Mikroinstrumente aus Nickel-Titan; article dated 1997; F&M 105, Copyright Carl Hanser Verlag; Munich, Germany.
Certified Translation of Netherlands Publication No. 9200491, published Jan. 18, 1993 (van Geer in Rikswijk).

* cited by examiner

*Primary Examiner* — Katherine Dowe
(74) *Attorney, Agent, or Firm* — Evans & Dixon, LLC; Joseph M. Rolnicki (57) ABSTRACT

A microsurgical instrument is constructed to an extremely small scale with serrations formed on opposed operative microsurgical surfaces of the instrument by electric discharge machining.

22 Claims, 10 Drawing Sheets

SURGICAL INSTRUMENT CONSTRUCTED BY ELECTRIC DISCHARGE MACHINING

This is a divisional patent application of patent application Ser. No. 10/167,914, filed Jun. 12, 2002, now U.S. Pat. No. 6,772,765.

BACKGROUND OF THE INVENTION (1) Field of the Invention

The present invention pertains to a surgical instrument that is constructed in an extremely small scale for use in microsurgery. In particular, the present invention pertains to a microsurgical instrument having a pair of operative surgical surfaces that are moved relative to each other in shearing or grasping procedures performed by the instrument, where the surgical instrument and its operative surgical surfaces are constructed by electric discharge machining.

(2) Description of the Related Art

Microsurgical instruments are those types of surgical instruments employed in performing surgical operations on extremely small and extremely delicate parts of the human anatomy, for example the tissues inside the human eye. There are many different types of microsurgical instruments. The more complex in construction and the most difficult to manufacture are microsurgical instruments that have at least one pair of operative surgical surfaces that move relative to each other in use of the instrument. By operative surgical surfaces what is meant is, for example, the opposed shearing surfaces of a scissors that have shearing edges that move across each other in a sheering operation performed by the instrument, or the opposed grasping surfaces of a forceps that move toward and away from each other in a grasping operation performed by the instrument. In the manufacturing of microsurgical instruments of this type, it is desirable that the scale of the instrument be as small as possible so that the introduction of the instrument to the surgical site is minimally invasive.

A typical microsurgical instrument is comprised of a manual handle that is similar in size and shape to a pen or pencil, which enables the instrument to be easily manipulated by the surgeon in one hand. An instrument head is secured to one end of the handle and the microsurgical forceps or a scissors tip projects from the instrument head. An example of this type of instrument is disclosed in U.S. Pat. No. 5,370,658, assigned to the assignee of the present invention and incorporated herein by reference.

Prior art microsurgical instrument tips of the type disclosed in the referenced patent often comprise a hollow, narrow tube projecting from the instrument head. A rod is received in the tube and the rod and tube are caused to reciprocate relative to each other in response to manual manipulation of some type of actuator on the instrument handle. The relative movement between the rod and tube operates the surgical instrument formed at the distal ends of the rod and tube. Where the surgical instrument is a forceps, the opposed jaws of the forceps are formed at the rod distal end and moving the tube over the rod or retracting the rod into the tube causes the forceps jaws to move toward each other. The reverse movements of the tube and rod cause the jaws to separate from each other. Where the surgical instrument is a scissors, one of the shear surfaces is formed at the distal end of the rod and the other shear surface is formed at the distal end of the tube. Moving the tube distal end toward the rod distal end causes the shear surfaces and their shearing edges to move toward and across each other.

As stated earlier, for microsurgical applications, the surgical instruments discussed above must be manufactured in an extremely small scale. In manufacturing the forceps discussed above, two pieces of wire stock would typically be ground down along their entire lengths until each piece was reduced to substantially half of its original thickness or width. Gripping surfaces would then be formed on the distal ends of the two pieces of wire stock by further grinding or cutting grooves across the previously ground surfaces of the wires. The two wire halves would then be welded or brazed together at their proximal ends and along an intermediate portion of their lengths. The thus formed forceps would then typically be polished.

In forming a scissors of the type discussed above, the scissor blade would first be cut from metal stock and one of the scissor blades would be welded or brazed to the distal end of the rod and the other of the scissor blades would be welded or brazed to the distal end of the tube. The operative surgical surfaces or the two shearing surfaces of the blades would then be ground forming shearing edges on the two surfaces. The rod and tube and the pair of blades attached thereto would then be polished to enhance their appearance.

The need for the final grinding step of the operative surgical surfaces of the instruments, i.e. the gripping surfaces of the forceps and the shearing surfaces of the scissors, limit the size to which a microsurgical instrument can be scaled. Due to the stresses exerted on the operative surgical surfaces of the instruments as the surfaces are ground, there must be a sufficient amount of material present in these areas of the instruments to withstand the grinding. Thus, the need to grind the material of the instrument tips to form the operative surgical surfaces of the microsurgical instruments limits the size to which the instruments can be reduced.

SUMMARY OF THE INVENTION

The present invention provides a novel method of constructing a microsurgical instrument as well as the microsurgical instrument constructed according to the method. The instrument has operative tips that are reduced in size compared to prior art microsurgical instruments. The microsurgical instrument of the invention is comprised of a handle assembly and an instrument head assembly that are basically the same as those of the prior art. However, the instrument tip is constructed according to a novel method and results in an instrument tip having a novel construction that is reduced in size from that of the prior art. Furthermore, the novel construction of the instrument tip requires fewer manufacturing steps than those of the prior art, resulting in decreased manufacturing costs.

The instrument handle and instrument head of the microsurgical instrument of the invention are basically the same as those described in U.S. Pat. No. 5,370,658, referenced earlier. Alternatively, other types of instrument handles and heads may be employed that result in relative reciprocating movement of an instrument tip rod through an instrument tip tube in response to manipulation of a manual actuator of the instrument handle by the surgeon's hand.

The instrument handle of the invention has an elongate length with an exterior configuration that is similar to that of a pen or pencil, enabling it to be comfortably held in the surgeon's hand. One or more lever arms are mounted on the handle exterior in positions where they can be easily manipulated by the surgeon's fingertips. A distal end of the handle is attached to the instrument head.

The instrument head proximal end is attached to the instrument handle distal end and a microsurgical instrument tip projects from the opposite distal end of the instrument head. In the preferred embodiment of the invention, the surgical instrument tip is comprised of an elongate, narrow rod mounted in an elongate, narrow tube for relative reciprocating movement between the rod and tube. The rod and tube project from the instrument head to distal ends of the rod and tube, with the distal end of the rod extending slightly beyond the distal end of the tube. The proximal end of one of the instrument tip rod and tube is mounted stationary in the instrument head. A mechanical connection is provided between the lever arm of the handle and the other of the instrument tip rod and tube, whereby manual manipulation of the level arm produces linear reciprocating movement between the rod and tube.

In the preferred embodiment of the invention the rod is secured stationary to the instrument head and the tube reciprocates over the rod toward and away from the rod distal end. The distal end of the instrument tip rod is formed as a scissors or forceps that operates in response to the linear reciprocating movement of the tube over the rod. The novel manner in which the distal end of the rod is formed as the scissor or forceps results in a novel construction of the microsurgical instrument that is reduced in size from prior art microsurgical instruments.

Each of the microsurgical instruments of the invention is formed from a blank of metal comprising a narrow, elongate shaft with opposite proximal and distal ends and a block of metal formed at the shaft distal end. The block and the shaft of the blank are one piece of metal. In the preferred embodiment, the shaft of the blank is straight and has a center axis between its opposite proximal and distal ends. The exterior surface of the shaft is cylindrical and is dimensioned with an exterior diameter determined to enable the shaft to reciprocate linearly through the interior bore of the instrument tube without any machining or manufacturing operations required on the exterior surface of the shaft.

In preparation for forming the operative surgical surfaces in the block at the distal end of the shaft, the blank is secured in a wire electric discharge machine by mounting the shaft to the machine adjacent the proximal end of the shaft which requires no machining. A first cutting operation is then performed in the block of the one piece metal blank by moving the wire of the wire electric discharge machine and the one piece blank relative to each other. The wire is moved through the block of the blank in an elongate parabolic path that is centered relative to the shaft center axis. This separates the block into two pieces, removing a large portion of the block from the remaining parabolic shaped portion of the block left on the shaft distal end. In the next manufacturing step, the blank is rotated slightly about the shaft center axis relative to the wire and the block of the blank is cut again by moving the wire and the block relative to each other. The wire is moved through the block a second time, cutting a serrated or grooved surface into one side of the block. The blank is then rotated again about the shaft center axis relative to the wire so that it is positioned rotated 90 degrees from its original position relative to the wire of the electric discharge machine. The block of the blank is cut again by moving the wire and the block relative to each other. The wire moves through the block cutting the block into the two separate blades of the surgical scissors while also cutting a slot axially through a portion of the center of the shaft from the shaft distal end. The two scissor blades are cut with one of the blades having the plurality of the serrations or the grooves on an operative surgical surface of the blade, thereby giving this operative surgical surface a serrated edge. With the third cut performed by the wire of the wire electric discharge machine, the machining of the operative surgical surfaces of the instrument, and in particular the cutting edges of the scissors blades, is complete and no further machining operations are required, thus eliminating the grinding step required in manufacturing prior art microsurgical scissors.

The machined instrument rod is then removed from the electric discharge machine and portions of the shaft distal end that were split by the wire of the electric discharge machine are bent slightly relative to each other. The bending positions the scissor blades where they are spaced from each other, opening a gap between the cutting edges of the two blades, but where the cutting edges will move across each other as the tube of the microsurgical instrument moves over the shaft. The shaft is then assembled to the microsurgical instrument with the cutting blades and adjacent portions of the distal end of the shaft projecting from the distal end of the instrument tube.

In operation of the instrument, the tube is moved distally over the shaft causing the distal end of the tube to move the two blades of the scissors toward and across each other in the cutting operation. Reversing the movement of the tube relative to the shaft causes the distal end of the tube to move away from the bent portions of the shaft and allows the scissor blades and the split portion of the shaft distal end to move to their original bent configurations separating the scissor blades from each other.

The microsurgical forceps is constructed in a similar manner to that of the scissors. The one piece metal blank is positioned in the electric discharge machine with the blank mounted to the machine at the shaft proximal end. A first cutting step is then performed in both the block and shaft of the blank by moving the wire of the wire electric discharge machine and the blank relative to each other. The wire is moved through the block of the blank forming one of the jaws of the forceps and then the wire is moved along the center axis of the shaft at the shaft distal end. The wire is then retracted along the center axis of the shaft and moves through the block of the blank again forming the second jaw of the forceps and cutting the block into two pieces before exiting the block. As the wire of the electric discharge machine forms each jaw of the forceps, it also forms serrations or gripping grooves in the opposed operative surgical surfaces of the forceps jaws. The blank is then rotated 90 degrees relative to the wire of the electric discharge machine and the wire is again moved through the block of the one piece blank, forming each of the jaws of the forceps with a tapered tip. The serrations or grooves formed in the operative surgical surfaces of the forceps by the wire of the electric discharge machine are complete following the cutting operation of the wire and no further machining of the surfaces, i.e., grinding, is needed.

The forceps shaft is assembled to the surgical instrument in the same manner as the scissors described earlier, with the shaft extending through the interior of the instrument tube. Linear reciprocating movement of the tube over the shaft of the forceps causes the jaws of the forceps to separate from each other and to move toward each other in a gripping operation.

By manufacturing the microsurgical instruments employing electric discharge machining as described above, the operative surgical surfaces of the instruments are formed in a single step by the cutting operation of the wire of the electric discharge machine and no additional manufacturing steps, i.e. grinding of the surfaces, is needed. In this way, the surgical instruments can be constructed to a much smaller scale than prior art instruments and with fewer manufacturing steps, thus decreasing the cost of manufacturing.

BRIEF DESCRIPTION OF THE DRAWINGS

Further features of the present invention are revealed in the following detailed description of the preferred embodiments of the invention and in the drawing figures wherein.

DESCRIPTION OF THE PREFERRED EMBODIMENTS

Figure 1:
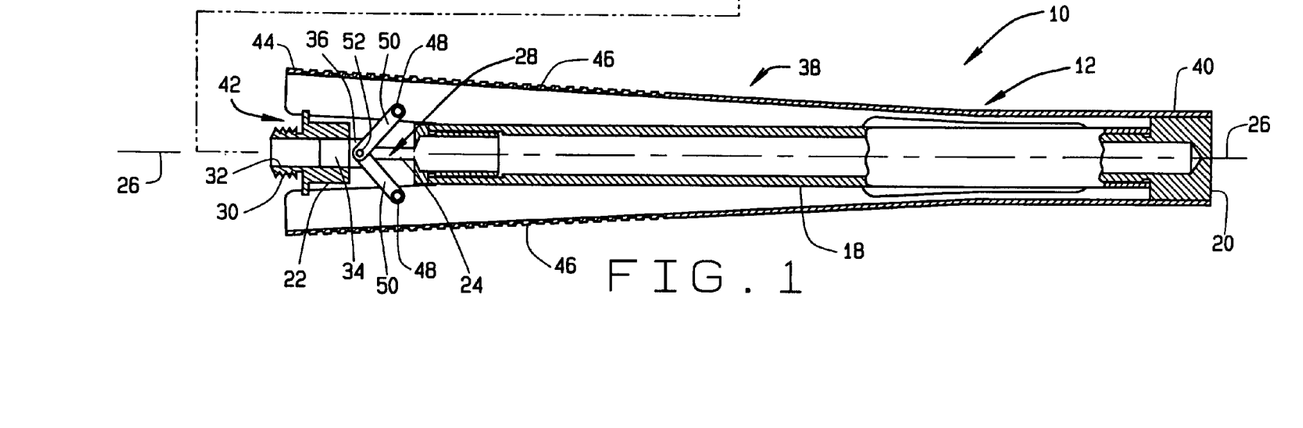
FIG. 1 is a sectioned view of the microsurgical instrument of the invention.

FIG. 1 shows the microsurgical instrument 10 of the present invention. The instrument is basically comprised of an instrument handle 12 and an instrument head 14 attached to the handle. A microsurgical instrument tip 16 projects from the instrument head 14. The novel features of the invention are provided on the microsurgical instrument tip 16. The handle 12 and instrument head 14 of the microsurgical instrument are basically the same as one of the embodiments disclosed in U.S. Pat. No. 5,370,658, assigned to the assignee of the present invention and incorporated herein by reference. Because the microsurgical instrument handle and head are known in the prior art, their construction and operation will be described only generally herein.

In the preferred embodiments of the invention, all of the component parts of the microsurgical instrument to be described are constructed of a material that is capable of being sterilized, preferably alloys of titanium or aluminum to reduce the instrument's weight. However, it should be understood that the preferences set forth herein are not intended to be limiting and the instrument of the invention may be constructed from a variety of materials suitable for the intended use of the instrument.

The instrument handle 12 is comprised of a center tubular column 18 having a narrow length with opposite rearward and forward ends. A rear plug 20 is press fit into the rearward end of the instrument column, or the right-hand end of the column as viewed in FIG. 1. A forward plug 22 is press fit into the opposite forward end of the handle column 18. The forward plug 22 is formed with a generally planer central web 26 that projects forward from the plug parallel to a center axis 26 of the microsurgical instrument. A slot 28 is formed through the central web and extends parallel to the instrument center axis 26. The central web 24 extends forward to a cylindrical attachment portion 30 of the forward plug that attaches the handle 12 to the instrument head 14. A cylindrical center bore 32 extends through the forward plug attachment portion 30 coaxially with the instrument center axis 26. A handle piston 34 is mounted in the forward plug center bore 32 for reciprocating movement in the bore along the instrument center axis 26. The handle piston 34 is provided with a flat flange 36 projecting rearwardly from the piston.

A resilient cylindrical sleeve 38 is assembled over the handle column 18 with a rearward end of the sleeve mounted on the handle column rearward plug 20. A pair of longitudinal slots 42 are cut in diametrically opposite sides of the sleeve and extend along a portion of the length of the sleeve from adjacent the sleeve rearward end 40 to the sleeve forward end 44. Only one of the slots 42 is visible in the cross section of FIG. 1. The slots 42 form the sleeve into a pair of resilient lever arms 46. The lever arms 46 are bent laterally outwardly away from the instrument center axis 26 to at rest positions of the arms shown in FIG. 1. The resiliency of the lever arms 46 enables them to be manually manipulated laterally or radially inwardly toward each other and toward the instrument center axis 26 in response to the fingers of the surgeon exerting a force on the exterior surfaces of the arms, and enables the arms to be resiliently biased outwardly away from each other and away from the instrument center axis in response to the force of the surgeon's fingers being removed from the exterior surface of the arms.

A pair of pivot pins 48 are secured to the interior surfaces of the lever arms and a pair of links 50 are mounted on the pivot pins. The links 50 extend from the pivot pins to the handle piston flange 36 and are each connected by a further pivot pin 52 to the handle piston flange. With the connection between the lever arms 46 and the handle piston 34 provided by the pair of links 50, it can be seen that manually moving the lever arms 46 inwardly toward each other will cause the pair of links 50 to push the handle piston 34 forwardly through the center bore 32 of the handle column forward plug 22. When the force is removed from the lever arms the resiliency of the lever arms 46 will cause them to move outwardly which in turn causes the pair of links 50 to pull the handle piston 34 back through the forward plug center bore 32 in a rearward direction.

The instrument head 14 is designed to perform a scissors cutting microsurgical operation. The instrument head 14 is comprised of a head housing 56 containing the component parts of the instrument. An internally screw threaded collar 60 connects the instrument head 14 to the instrument handle forward plug 22. The housing 56 has a cylindrical interior bore 62 that extends through the length of the housing and is coaxial with the instrument center axis 26. A head piston assembly 64 is mounted in the housing center bore 62 for axial reciprocating movement through the bore. A rearward end of the head piston assembly 64 engages against the handle piston 34 in the instrument handle. The head piston assembly 64 has a slot 66 through an intermediate portion of the piston assembly. A coil spring 68 engages against a forward portion of the head piston assembly 64 and against an annular shoulder 70 formed in the housing interior surface surrounding the housing center bore 62. The spring 68 biases the head piston assembly 64 rearwardly or to the right as viewed in FIG. 1. A pair of set screws 72 are threaded into a pair of opposed screw threaded holes and engage against opposite sides of the proximal or rearward end of a narrow, elongate rod 76 that is a part of the microsurgical instrument tip 16 of the invention. The set screws 72 hold the rod 76 stationary relevant to the instrument head 14. The microsurgical instrument tip 16 is also comprised of a narrow, elongate tube 78 that is mounted on the rod 76 for reciprocating movement over the exterior surface of the rod. The proximal or rearward end of the tube 78 is mounted in the forward end of the head piston assembly 64. The tube 78 reciprocates axially along the instrument center axis 32 and along the length of the rod 76 in response to axial reciprocating movement of the head piston assembly 64. Thus, manual manipulation of the instrument handle lever arms 46 toward and away from the instrument center axis 26 reciprocates the handle piston 34 in the handle center bore 32 which in turn causes reciprocation of the head piston assembly 64 in the instrument head center bore 62. The reciprocation of the head piston assembly also reciprocates the tube 78 over the length of the rod 76.

The novel features of the microsurgical instrument tip 16 of the invention are in the construction of the distal end of the elongate rod 76 and in its method of construction.

Figures 2, 3:
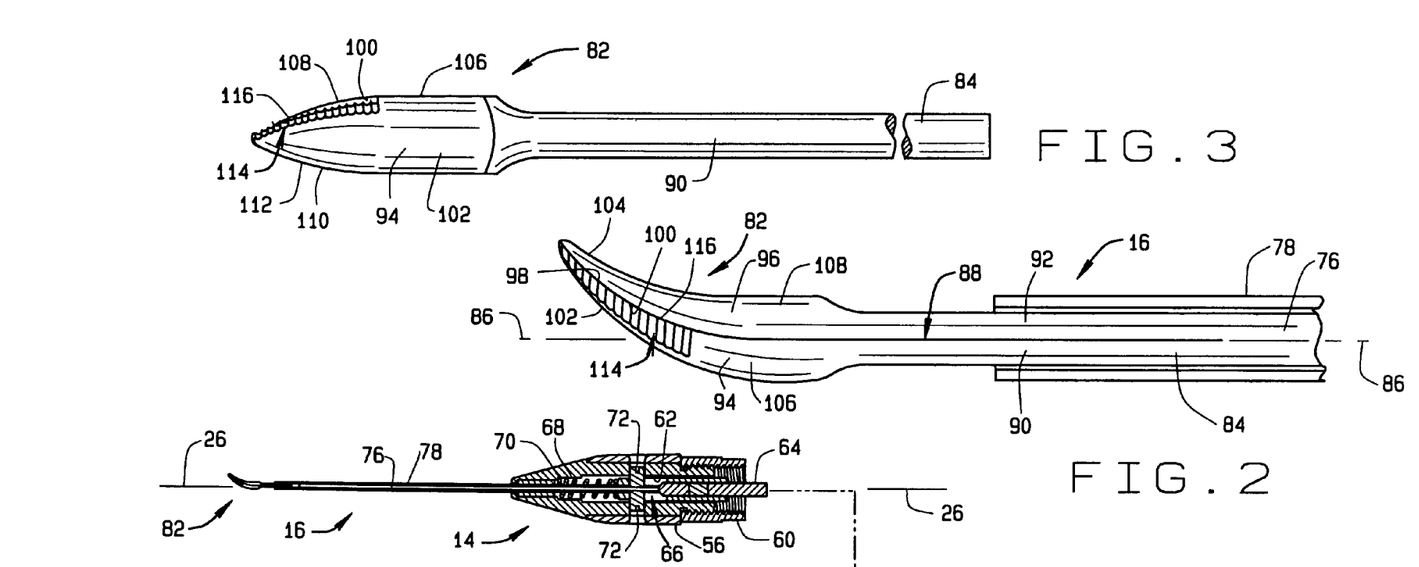
FIG. 2 is an enlarged partial plan view of the microsurgical instrument tip.
FIG. 3 is a side view of the instrument tip shown in FIG. 2.
Figure 4:
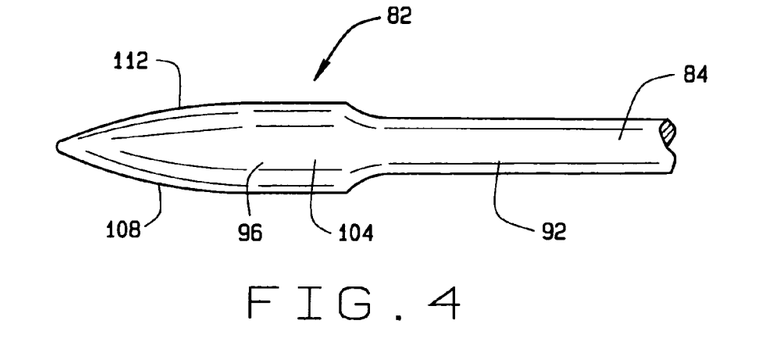
FIG. 4 is an opposite side view of the instrument tip shown in FIG. 3.
Figure 5:
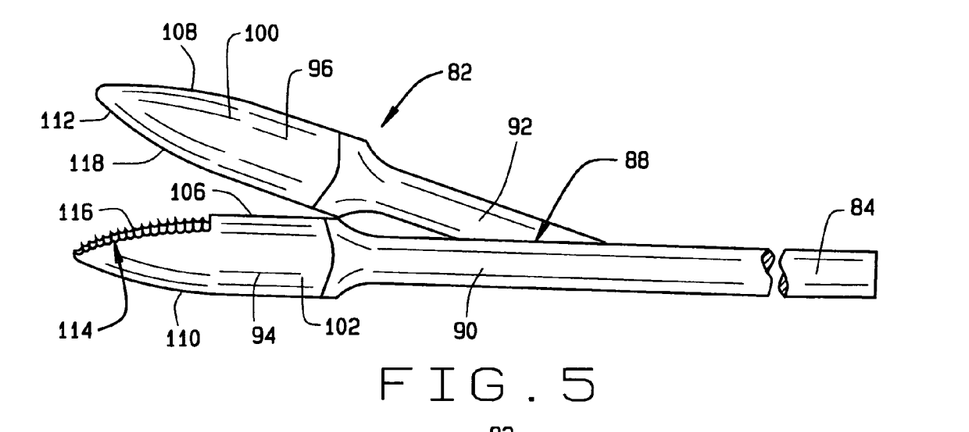
FIG. 5 is a view of the instrument tip similar to that of FIG. 3, but with the operative surgical surfaces moved relative to each other.

FIGS. 2 through 5 show the microsurgical scissors of the invention formed at the distal end of the rod 76 of the microsurgical instrument. FIGS. 2, 3 and 4 show the scissors in its closed position and FIG. 5 shows the scissors in its open position. The scissors 82 comprise a shaft 84 that has a cylindrical exterior surface and is an extension of the distal end of the instrument rod 76. The shaft 84 has a center axis 86 and a slot 88 is formed in the shaft intersecting the center axis. The slot 88 does not extend entirely through the length of the shaft 84, but begins at an intermediate portion of the shaft and extends to the shaft distal end dividing the shaft into a pair of resilient spring arms 90, 92 and dividing the distal end of the shaft into a pair of scissor blades 94, 96. In the preferred embodiment of the invention, the slot 88 is formed by a wire electric discharge machine, as will be explained.

The slot 88 formed through the distal end of the shaft 84 forms a pair of opposed surfaces 98, 100 of the two scissor blades. The two scissor blades also have back surfaces 102, 104 on opposite sides of the blades from their opposed surfaces. Each of the blades also has a top surface 106, 108 and an opposite bottom surface 110, 112. A plurality of serrations or grooves 114 are formed into a portion of the top surface 106 of one of the scissor blades 94. These serrations 104 and the top surface of the blade form a serrated edge 106 at the edge of the blade where the top surface 106 joins the opposing surface 98 of the one blade 94. The serrations 114 and the top surface of the one blade 94 function as the operative microsurgical surface of the blade. The operative microsurgical surface of the other, opposite blade 96 is its bottom surface 112. The edge 118 of the opposite blade 96 where its bottom surface 112 joins its opposing surface 100 moves past the serrated edge 116 of the one scissor blade 94 in the cutting operation of the scissors. The cutting edges 116, 118 of both of the scissor blades 94, 96 are formed solely by electric discharge machine cutting of the scissor blades. No grinding of the operative microsurgical surfaces 106, 112 of the blades or of their cutting edges 116, 118 is needed after the blades have been cut by electric discharge machining. Furthermore, the small tolerances achievable by electric discharge machining enables the microsurgical scissors 82 of the invention to be manufactured to a reduced scale compared to prior art microsurgical instruments.

FIGS. 6, 7, 8 and 9 illustrate schematically the novel method of making the microsurgical scissors 82 of the invention.

Figure 6:
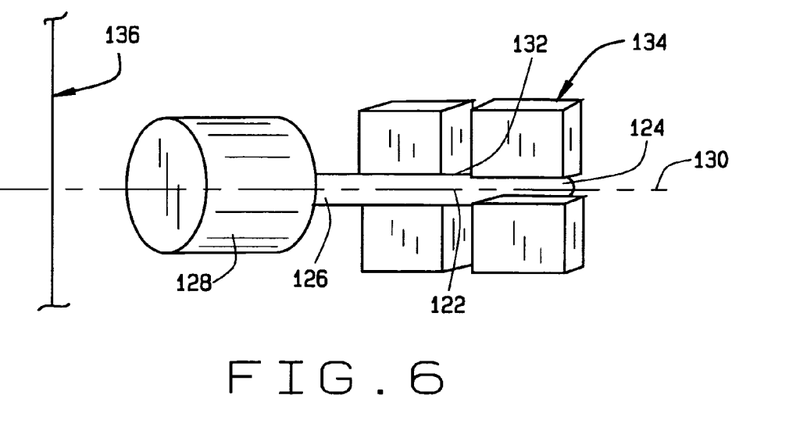
FIG. 6 is a schematic representation of a blank of metal held by a wire electric discharge machine prior to cutting of the blank to produce the instrument tip.

The one piece microsurgical scissors 82 of the invention is formed from a blank of metal comprising a narrow, elongate shaft 122 with opposite proximal 124 and distal 126 ends with a block 128 of metal formed at the shaft distal end. The block 128 and the shaft 122 of the blank are one piece of metal. The shaft 122 is straight and has a center axis 130 and a cylindrical exterior surface 132. The exterior surface 132 of the shaft is dimensioned with an exterior diameter determined to enable the shaft to reciprocate linearly through the interior bore of the instrument tube 78 without any machining or manufacturing operations required on the exterior surface of the shaft.

Figure 7:
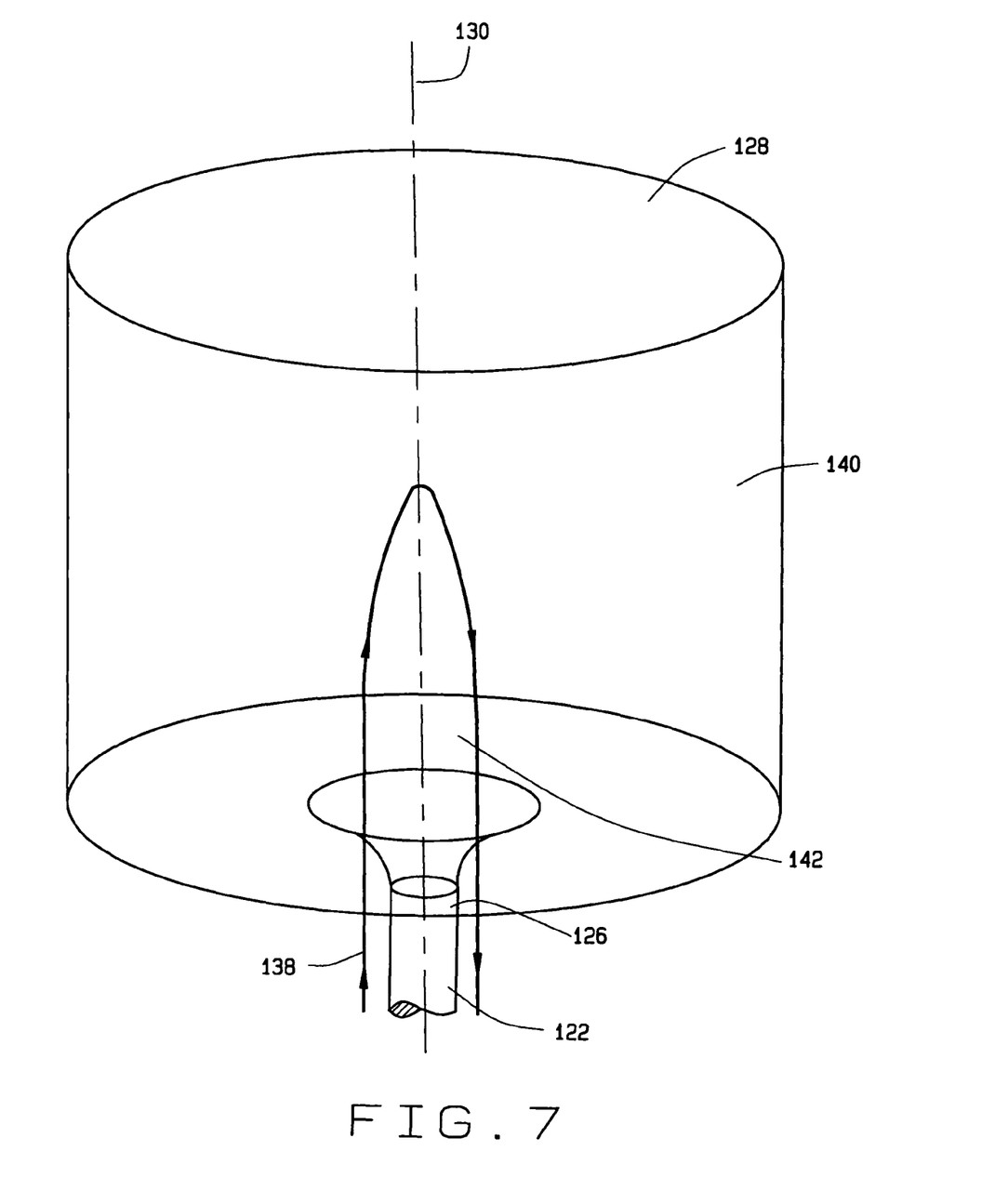
FIG. 7 is a schematic representation of the method of producing the instrument tip of FIG. 3.

In preparation for forming the operative surgical surfaces in the block 128 at the distal end of the shaft 122 of the blank, the blank is secured in a wire electric discharge machine by mounting the shaft 122 in a chuck 134 of the machine adjacent to the proximal end of the shaft which requires no machining. A schematic representation of a wire electric discharge machine is shown in FIG. 6. Prior to the first machining step, the wire 136 of the electric discharge machine is positioned in the same plane as the shaft center axis 130 and is oriented at a slight angle, preferably an 18 degree forward angle relative to the shaft axis 130. A first cutting operation is then performed in the block 128 of the one piece metal blank by moving the wire 136 of the electric discharge machine and the one piece blank relative to each other. FIG. 7 shows the path of the wire 136 relative to the block 128 and shaft 122 of the blank from the point of view of looking down the wire center axis. The wire 136 is moved through the blank block 128 in an elongate parabolic path 138 that is centered relative to the shaft center axis 130. This separates the blank block 128 into two pieces, removing a large portion 140 of the block from the remaining parabolic shaped portion 142 of the block left on the shaft distal end 126.

Figure 8:
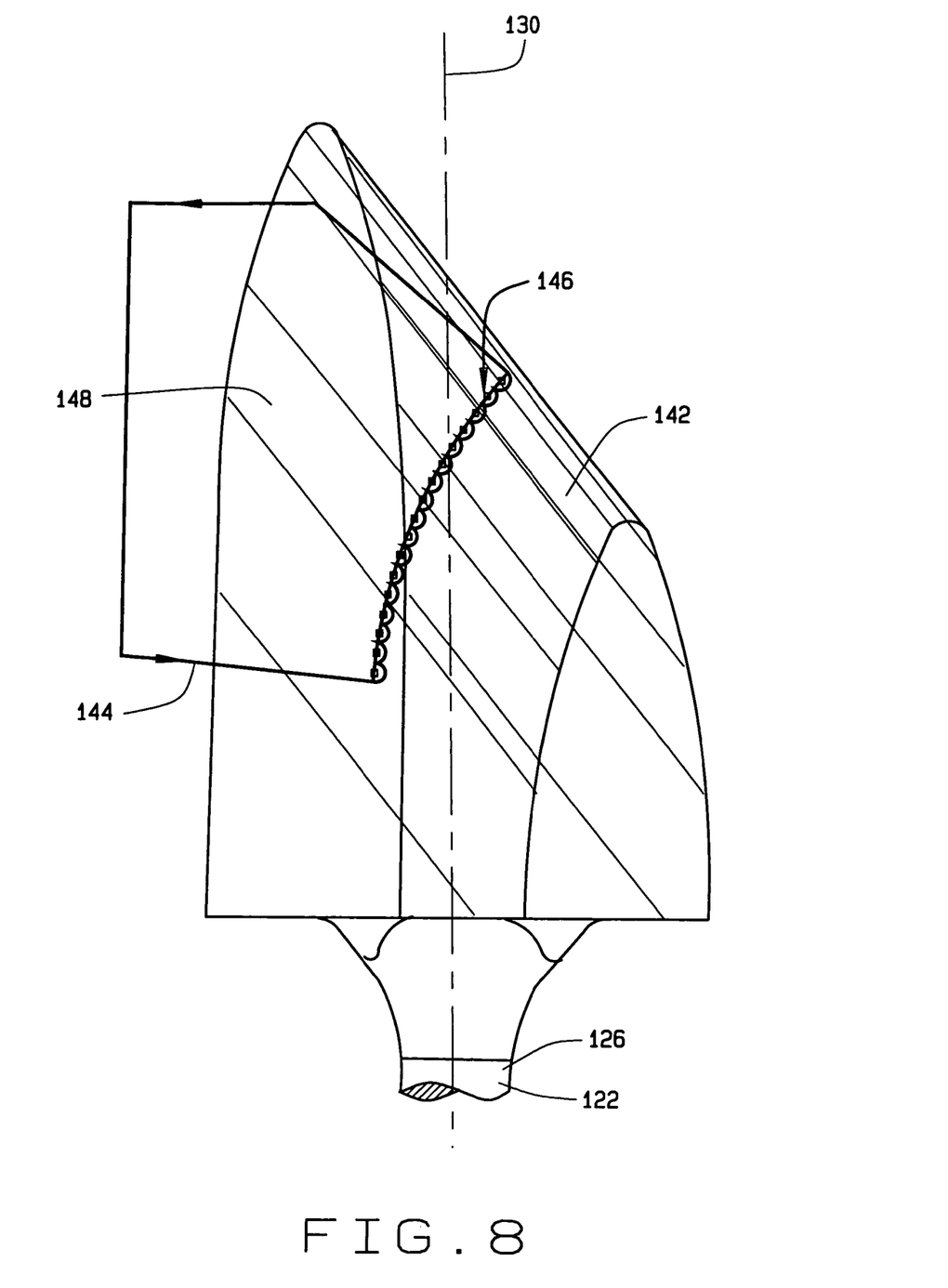
FIG. 8 is a schematic representation of a further step employed in forming the instrument tip of FIG. 3.

In the next manufacturing step shown in FIG. 8, the remaining blank with the parabolic-shaped portion 142 of the block is rotated slightly about the shaft center axis 130 relative to the electrical discharge machine wire 136. In the preferred embodiment, the remaining portion of the blank is rotated 15 degrees relative to the wire 136. The remaining portion 142 of the block is then cut again by moving the wire 136 and the block portion 142 relative to each other. The wire path 144 shown in FIG. 8 is from the point of view of looking down the center axis of the wire. The wire is moved through the remaining block portion 142 a second time cutting a serrated or grooved surface 146 into one side of the block portion 142 and separating a second piece 148 from the block portion.

Figure 9:
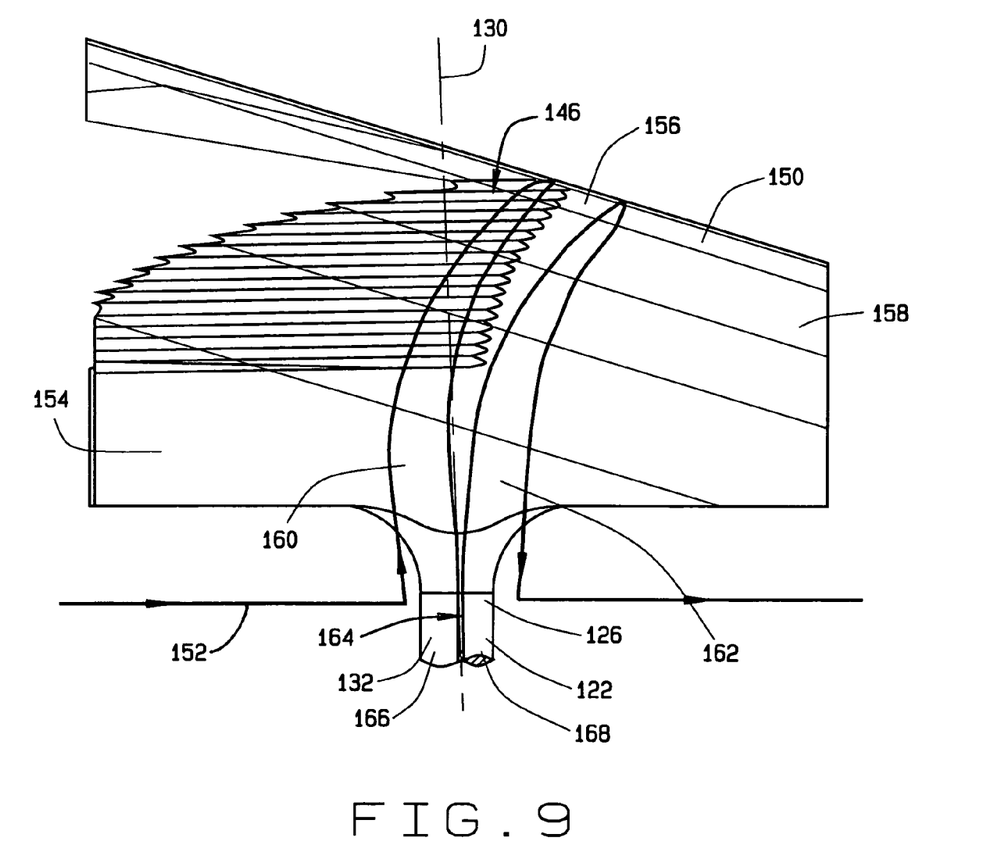
FIG. 9 is a schematic representation of a still further step employed in forming the surgical instrument tip of FIG. 3.

FIG. 9 illustrates the next manufacturing step performed on the remaining block portion with the serrated surface 150. Prior to the cutting operation, the blank with the serrated surface block portion 150 is again rotated about the shaft center axis 130. In the preferred embodiment the blank is rotated 90 degrees from the original position of the blank in the electric discharge machine before the first cutting operation took place. The serrated surface block portion 150 is then cut by moving the wire 136 of the electric discharge machine and the block portion 150 relative to each other. FIG. 9 shows the third cut path 152 of the wire from the point of view of looking down the center axis of the wire. The wire moves through the serrated surface block portion 150 cutting away three separate pieces 154, 156, 158 as it cuts the two separate blades 164, 166 of the microsurgical scissors and the slot 164 separating the scissor blades and the scissors' resilient spring arms 166, 168. From the wire cut path 152 shown in FIG. 9 it can be seen that first one of the scissor blades 160 is cut and then the slot 164 is formed in the shaft 122 by the wire 136 moving parallel to the shaft center axis 130 toward the shaft proximal end, and then reversing its path moving parallel to the shaft center axis toward the shaft distal end and the serrated surface block portion 150. The wire 136 then cuts the second scissors blade 162 from the serrated surface block portion. The two scissor blades 160, 162 are cut with the one blade 160 having the plurality of serrations 146 on an operative surgical surface 170 of the blade, thereby giving this operative surgical surface a serrated edge 172. The operative surgical surface of the other scissors blade 162 shown in FIG. 9 is on the opposite side of the blade shown. With the third cut performed by the wire of the electric discharge machine, the machining of the operative surgical surfaces of the instrument, and in particular the cutting edges of the scissors blades is complete and no further machining operations are required, thus eliminating the grinding step required in the manufacturing of prior art microsurgical scissors.

Figure 10:
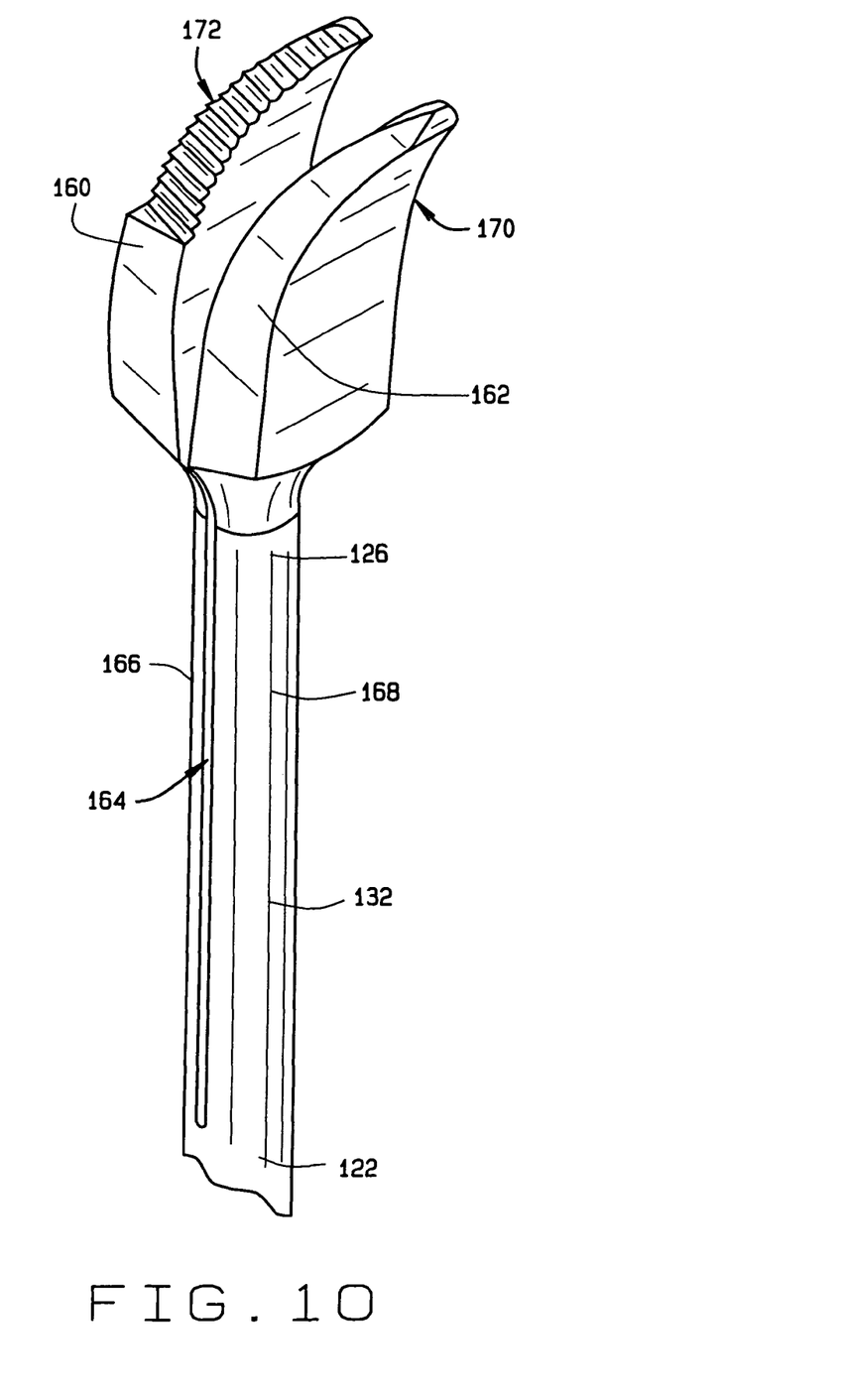
FIG. 10 is an enlarged partial perspective view of the instrument tip formed according to the method steps illustrated in FIGS. 7-9.

FIG. 10 shows the machined instrument rod removed from the electric discharge machine. With the machining of the rod completed, the shaft distal ends that were split by the wire of the electric discharge machine to form the spring arms 166, 168 are then bent slightly relative to each other. Each of the spring arms 166, 168 is bent along the plane containing the slot 164 in directions away from each other. The scissors blades 160, 162 are then bent toward each other to position the blades relative to each other as shown in FIG. 2. The bending positions the scissor blades where they are spaced from each other with there being a gap between the cutting edges of the two blades, but where the cutting edges will move across each other as the tube 78 of the microsurgical scissors moves over the shaft. The shaft is then assembled to the microsurgical instrument with the cutting blades and the spring arms at the distal end of the shaft projecting from the tube distal end.

In operation of the instrument, the shaft 122 of the blank becomes the rod 76 of the instrument shown in FIG. 1. The rod 76 is mounted in the interior of the tube 78 with the proximal end of the rod being fixed to the instrument head 14 by the opposed pair of set screws 72. On manual manipulation of the lever arms 46, the tube 78 is caused to move distally over the exterior surface of the rod 76 causing the tube distal end to move toward the two spring arms 90, 92 of the scissors. This causes the two spring arms to move toward each other and also causes the scissors blades 94, 96 to move toward and across each other in the cutting operation. The serrated edge 116 and the opposed cutting edge 118 of the two scissors blades perform the cutting operation. Releasing the two lever arms 46 causes the tube to reverse its movement relative to the rod 76. The tube distal end is moved away from the two spring arms 90, 92 allowing the resiliency of the spring arms to move the two scissors blades 94, 96 away from each other to the at rest positions of the two spring arms shown in FIG. 5 where the two scissor blades are separated from each other.

Figure 11:
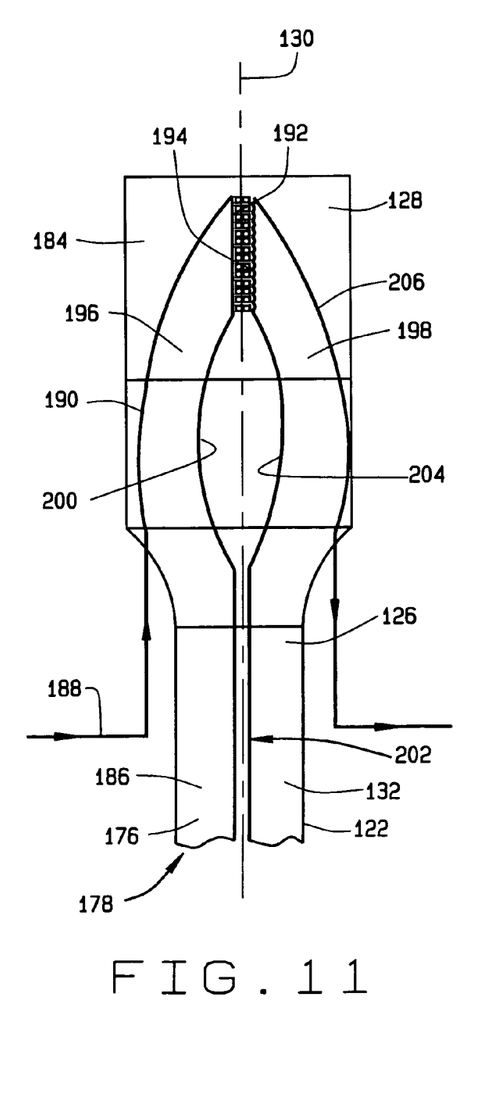
FIG. 11 is a schematic representation of the method employed in forming a further embodiment of the instrument tip.

The microsurgical forceps is constructed in a similar manner to that of the scissors. The forceps is formed from a one-piece metal blank similar to the blank of the scissors. The forceps blank is shown schematically in FIG. 11 and is comprised of a blank shaft 176 having opposite proximal 178 and distal 180 ends and a center axis 182. A block of metal 184 is formed as one piece with the shaft 176 at the shaft's distal end 180. In the preferred embodiment, the shaft 176 has an exterior surface 186 that is dimensioned to be received in the tube 78 of the microsurgical instrument for reciprocating movement of the shaft through the tube. The blank comprised of the shaft 176 and the block 184 of metal is positioned in the chuck of the electric discharge machine in the same manner as the blank of the scissors described earlier. The forceps blank is positioned relative to the wire of the electric discharge machine where the shaft center axis 182 is perpendicular to the wire. FIG. 11 shows the first path traveled by the wire of the electric discharge machine from the point of view of looking downward along the center axis of the wire. The first cutting step is performed in both the block 184 and the shaft 176 by moving the wire of the electric discharge machine and the blank relative to each other. The wire is moved through the block 184 of the blank first forming the back surface 190 of one of the block jaws. The wire then moves through the block 184 cutting the opposed operative microsurgical gripping surfaces 192, 194 of the one jaw 196 and the opposite jaw 198 of the forceps. The wire then moves through the block 184 cutting the one jaw opposing surface 200 that opposes the opposite jaw, and then moves through the shaft 176 in a path parallel to the shaft center axis 182 cutting a slot 202 through the center of the shaft. The wire then moves through the block 184 cutting the opposing surface 204 of the second jaw 198 of the forceps and then moves through the previously formed opposing operative gripping surfaces 192, 194 of the forceps. The wire then moves through the block 184 forming the back surface 206 of the second jaw cutting the block into two pieces before exiting the block.

Figure 14:
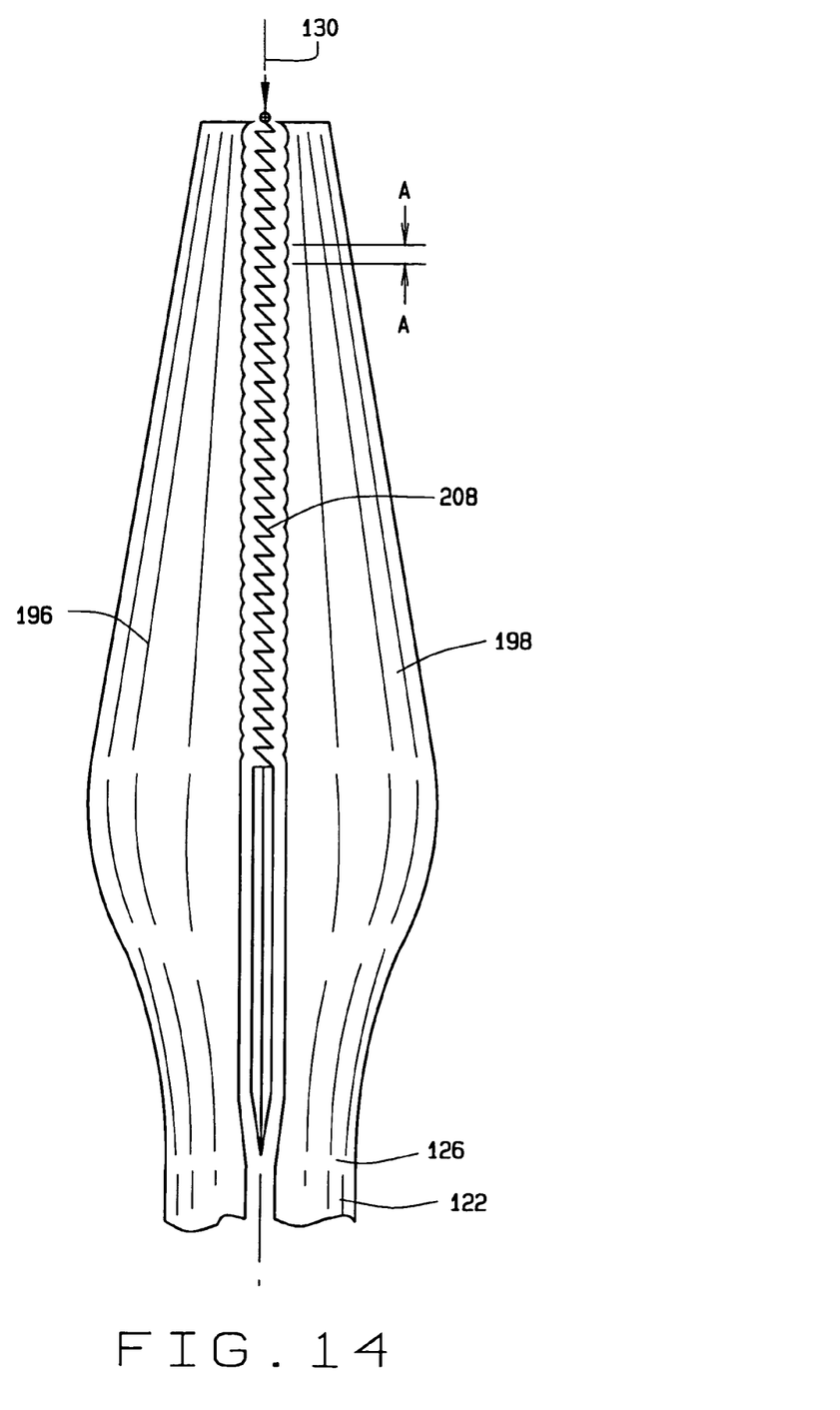
FIG. 14 is a schematic representation of the method employed in forming the forcep operative surgical surfaces of the instrument tip.
Figure 15A:
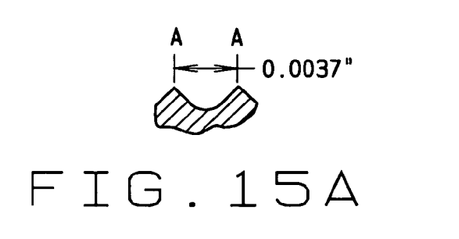
FIGS. 15a-15c are enlarged partial views of serrations formed on the operative surgical surfaces of the instrument tip.
Figure 15B:
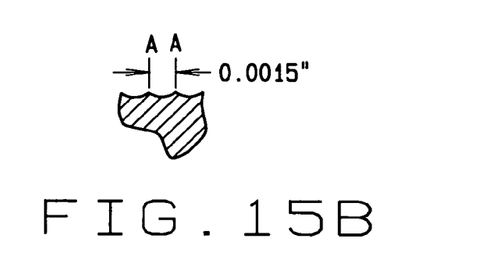
Figure 15C:
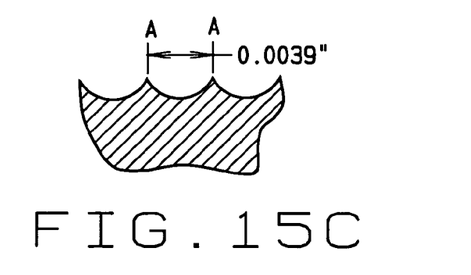
Figure 16A:
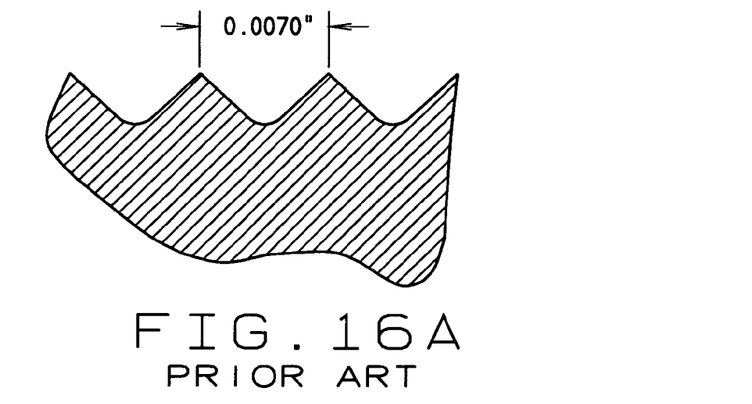
FIGS. 16a and 16b are enlarged partial views of prior art ground serrations.
Figure 16B:
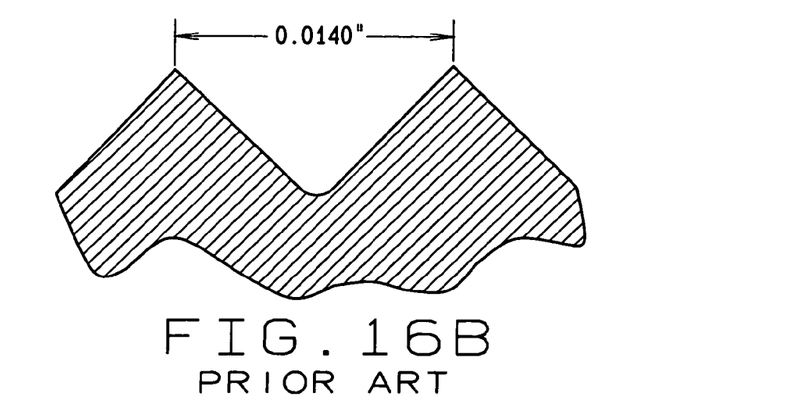

FIG. 14 shows one pattern that the wire of the electric discharge machine path can follow in forming the opposed operative gripping surfaces 192, 194 of the forceps jaws. FIG. 14 is a view of the wire path looking down the center axis of the wire. As shown in FIG. 14, the series of serrations 208 that make up the opposed gripping surfaces can be formed with the distance A-A between adjacent peaks of each serration being smaller than the diameter of the wire of the electric discharge machine. In the preferred embodiment of the invention, the width A-A of each serration between adjacent peaks of the serrations can be formed in a range of 0.0015 to 0.0039 of an inch as shown in FIGS. 15a-15c. The smallest serrations can be formed by the conventional grinding process typically range between 0.0070 and 0.0140 of an inch as shown in FIGS. 16a and 16b. Furthermore, the serrations 208 formed by the wire electric discharge machine are finished operative microsurgical surfaces that do not require any further machining operations, for example the grinding operation of the prior art.

Figure 12:
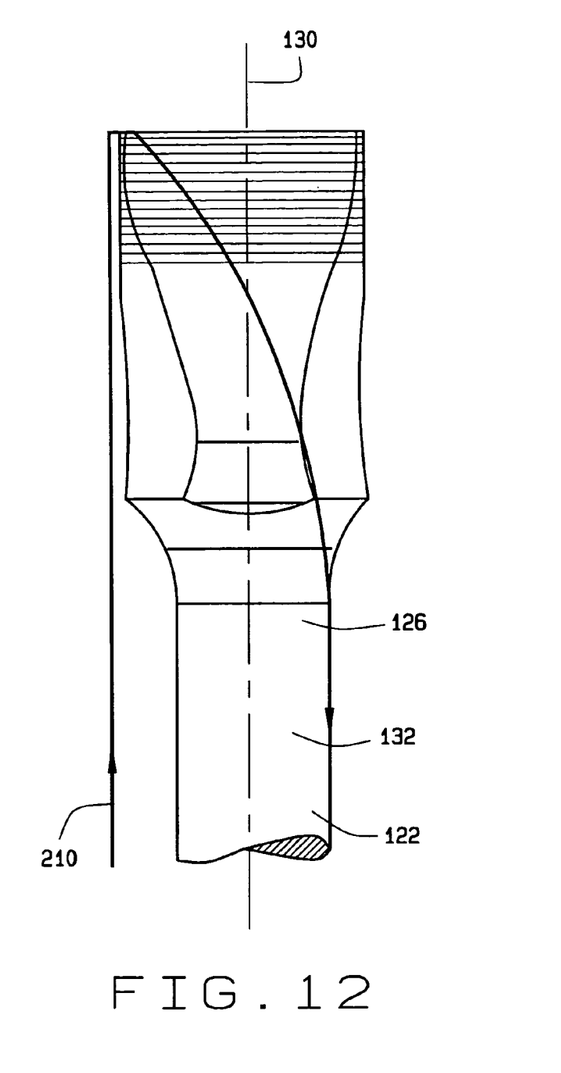
FIG. 12 is a schematic representation of a further step in forming the instrument tip of FIG. 11.
Figure 13:
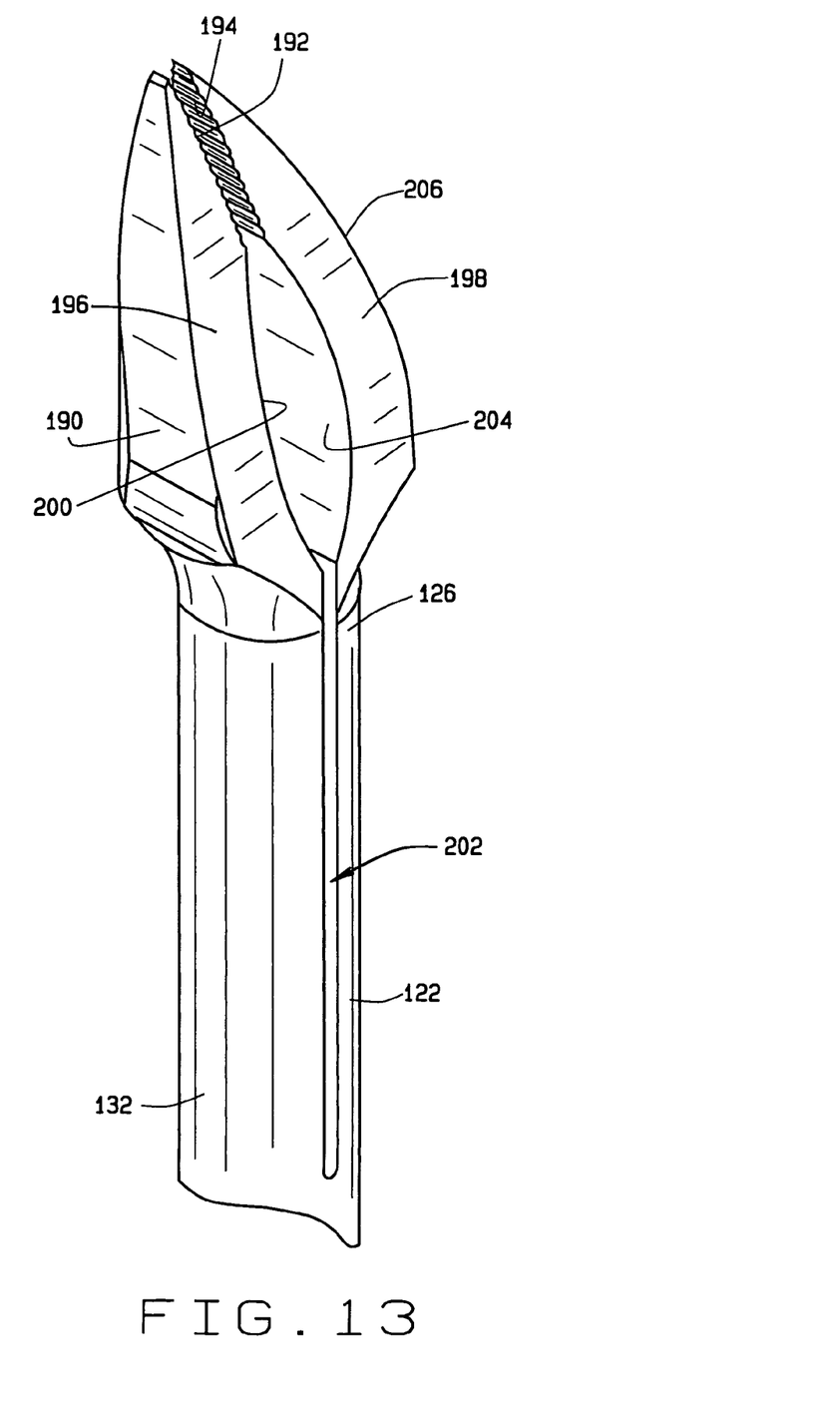
FIG. 13 is an enlarged partial perspective view of the instrument tip formed according to the method illustrated in FIGS. 11 and 12.

In the next machining step, the shaft 176 of the blank is rotated 90 degrees relative to the wire of the electric discharge machine and the wire is again moved through the block 184 of the one-piece blank. FIG. 12 shows the second cutting path 210 of the wire looking down the center axis of the wire. The wire is moved through the block of the blank along the path 210 shown in FIG. 12 forming each of the jaws of the forceps with a tapered tip. With completion of the second cutting path 210 of the wire, the machining of the forceps is complete except for a polishing step if desired. FIG. 13 shows the completed forceps produced from the two cutting steps of the wire described above.

The forceps shaft 176 is assembled to the surgical instrument in the same manner as the scissors described earlier, with the shaft 176 extending through the interior of the instrument tube 78 and the proximal end of the shaft being secured stationary to the instrument by the opposed pair of set screws 72. Linear movement of the tube 78 over the shaft 176 toward the pair of jaws 196, 198 causes the jaws to move toward each other to perform a gripping operation between the pair of operative gripping surfaces 192, 194 of the jaws. The reversed movement of the tube 78 over the shaft 176 allows the resiliency of the shaft material to separate the jaws from each other.

By manufacturing the microsurgical instruments employing electric discharge machining as described above, the operative surgical surfaces of the instruments are formed in one piece by the cutting operation of the wire of the electric discharge machine. Furthermore, no additional manufacturing steps, i.e. grinding of the operative surgical surfaces, is needed. In this way, the surgical instruments can be constructed to a much smaller scale than prior art instruments and with fewer manufacturing steps, thus decreasing the cost of manufacturing.

While the present invention has been described by reference to specific embodiments, it should be understood that modifications and variations of the invention may be constructed without departing from the scope of the invention defined in the following claims.

What is claimed is:

1. A microsurgical instrument comprising:
   first and second operative microsurgical surfaces;
   means for manually moving the first and second operative microsurgical surfaces toward and away from each other; and
   at least one of the operative microsurgical surfaces having a series of serrations and each serration having adjacent peaks and a width dimension between the adjacent peaks that is smaller than 0.007 of an inch.

2. The microsurgical instrument of claim 1, further comprising:
   each serration having a width dimension between the adjacent peaks of at most 0.0039 of an inch.

3. The microsurgical instrument of claim 1, further comprising:
   each serration having a width dimension between the adjacent peaks in the range of 0.0015 of an inch to 0.0039 of an inch.

4. The microsurgical surgical instrument of claim 1, further comprising:
   the series of serrations being a wire electric discharge machined surface.

5. The microsurgical instrument of claim 1, further comprising:
   the first and second operative microsurgical surfaces being on a pair of opposed forcep jaws.

6. The microsurgical instrument of claim 5, further comprising:
   the pair of forcep jaws being connected to an elongate rod with the pair of forcep jaws projecting from a distal end of the rod.

7. The microsurgical instrument of claim 6, further comprising:
   the pair of forcep jaws and the rod being formed from a single piece of material.

8. The microsurgical instrument of claim 6, further comprising:
   a slot formed into the rod at the rod distal end, the slot separating the pair of forcep jaws.

9. The microsurgical instrument of claim 6, further comprising:
   the pair of forcep jaws having been formed by wire electric discharge machining.

10. The microsurgical instrument of claim 6, further comprising:
    the pair of forcep jaws having been formed solely by wire electric discharge machining.

11. The microsurgical instrument of claim 6, further comprising:
    a slot formed in the rod at the rod distal end, the slot forming a pair of resilient spring arms at the rod distal end that connect the pair of forcep jaws to the rod.

12. The microsurgical instrument of claim 1, further comprising:
    the first and second operative microsurgical surfaces being on a pair of opposed scissor blades.

13. The microsurgical instrument of claim 12, further comprising:
    the pair of scissor blades being connected to an elongate rod with the pair of scissor blades projecting from a distal end of the rod.

14. The microsurgical instrument of claim 13, further comprising:
    the pair of scissor blades and the rod being formed from a single piece of material.

15. The microsurgical instrument of claim 13, further comprising:
    a slot formed in the rod at the rod distal end, the slot separating the pair of scissor blades.

16. The microsurgical instrument of claim 13, further comprising:
    the pair of scissor blades having been formed by wire electric discharge machining.

17. The microsurgical instrument of claim 13, further comprising:
    the pair of scissor blades having been formed solely by wire electric discharge machining.

18. The microsurgical instrument of claim 13, further comprising:
    a slot formed in the rod at the rod distal end, the slot forming a pair of resilient spring arms at the rod distal end that connect the pair of scissor blades to the rod.

19. A microsurgical instrument comprising:
    an elongate rod having opposite proximal and distal ends;
    a slot in the rod distal end forming a pair of resilient spring arms projecting from the rod;
    a pair of opposed, operative microsurgical surfaces on the pair of spring arms;
    the slot, the pair of spring arms, and the pair of operative microsurgical surfaces having been formed by electric discharge machining in a single piece of material;
    the pair of operative microsurgical surfaces being a pair of forcep jaws;
    the pair of forcep jaws having opposed serrated surfaces; and,
    the serrated surfaces having serrations with adjacent peaks and width dimensions between the adjacent peaks of the serrations that are smaller than 0.007 of an inch.

20. The microsurgical instrument of claim 19, further comprising:
    the pair of forcep jaws opposed serrated surfaces having been formed solely by electric discharge machining.

21. A microsurgical instrument comprising:
    an elongate rod having opposite proximal and distal ends;
    a slot in the rod distal end forming a pair of resilient spring arms projecting from the rod;
    a pair of opposed, operative microsurgical surfaces on the pair of spring arms;
    the slot, the pair of spring arms, and the pair of operative microsurgical surfaces having been formed by electric discharge machining in a single piece of material;
    the pair of operative microsurgical surfaces being a pair of scissor blades;
    the pair of scissor blades having opposed serrated edges; and, the serrated edges having serrations with adjacent peaks and width dimensions between the adjacent peaks of the serrations that are smaller than 0.007 of an inch.

22. The microsurgical instrument of claim 21, further comprising:
the pair of scissor blades opposed serrated edges having been formed solely by electric discharge machining.

* * * * *